US008320525B2

(12) United States Patent
Khouri

(10) Patent No.: US 8,320,525 B2
(45) Date of Patent: Nov. 27, 2012

(54) DIGITAL RADIOGRAPHY SENSORS

(76) Inventor: Louie Khouri, New York, NY (US)

( * ) Notice: Subject to any disclaimer, the term of this patent is extended or adjusted under 35 U.S.C. 154(b) by 192 days.

(21) Appl. No.: 12/670,899

(22) PCT Filed: Jul. 28, 2008

(86) PCT No.: PCT/US2008/071344
§ 371 (c)(1),
(2), (4) Date: Jun. 17, 2010

(87) PCT Pub. No.: WO2009/018211
PCT Pub. Date: Feb. 5, 2009

(65) Prior Publication Data
US 2010/0254518 A1 Oct. 7, 2010

Related U.S. Application Data

(60) Provisional application No. 60/952,309, filed on Jul. 27, 2007.

(51) Int. Cl.
H05G 1/64 (2006.01)
(52) U.S. Cl. .................. 378/98.8; 378/191; 250/370.09
(58) Field of Classification Search ................. 378/98.8, 378/189, 191; 250/370.09
See application file for complete search history.

(56) References Cited

U.S. PATENT DOCUMENTS

| 324,444 | A | 8/1885 | Wolf | |
|---|---|---|---|---|
| 521,429 | A | 6/1894 | Bessonette | |
| 4,423,919 | A | 1/1984 | Hillis | |
| 5,691,539 | A | 11/1997 | Pfeiffer | |
| 6,030,119 | A | 2/2000 | Tachibana et al. | |
| 6,169,781 | B1 * | 1/2001 | Doebert et al. | 378/98.8 |
| 6,320,934 | B1 * | 11/2001 | Carroll et al. | 378/98.8 |
| 6,527,442 | B2 | 3/2003 | Carroll | |
| 6,652,141 | B1 | 11/2003 | Cianciosi | |
| 7,150,424 | B2 | 12/2006 | Hopper | |
| 7,281,847 | B2 * | 10/2007 | Kokkaliaris et al. | 378/189 |
| 7,311,526 | B2 * | 12/2007 | Rohrbach et al. | 439/39 |
| 7,563,026 | B2 * | 7/2009 | Mandelkern et al. | 378/191 |
| 2006/0166161 | A1 | 7/2006 | Rose | |
| 2007/0134061 | A1 | 6/2007 | Nance | |

* cited by examiner

Primary Examiner — Allen C. Ho
(74) Attorney, Agent, or Firm — Harness, Dickey & Pierce, PLC

(57) ABSTRACT

A new and improved digital sensor assembly for use in a filmless radiography system is disclosed. The sensor is configured to be universal in that it can be rotated about a cable connection thereby allowing the sensor to be used both vertically and horizontally in the oral cavity. The rotatability of the sensor allows it to fit comfortably and close to a target area in an intraoral cavity. By providing a comfortable relative fit to the target area, the sensor is ergonomically improved, in terms of its comfort and feel to a dental patient. Alternative sensor assembly embodiments disclosed herein relate to quick disconnect-type coupling arrangements between the sensor body and the sensor cable.

19 Claims, 5 Drawing Sheets

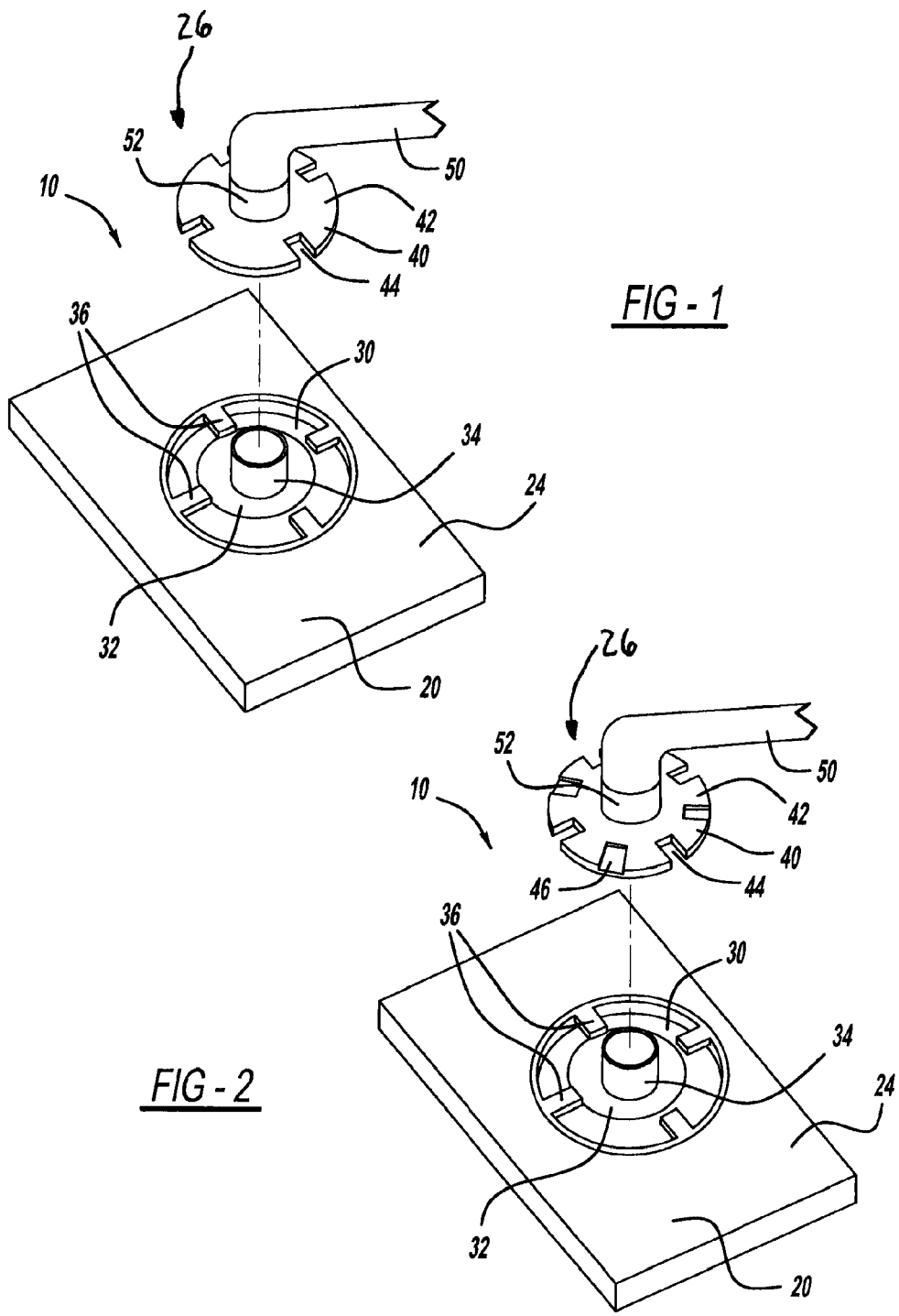

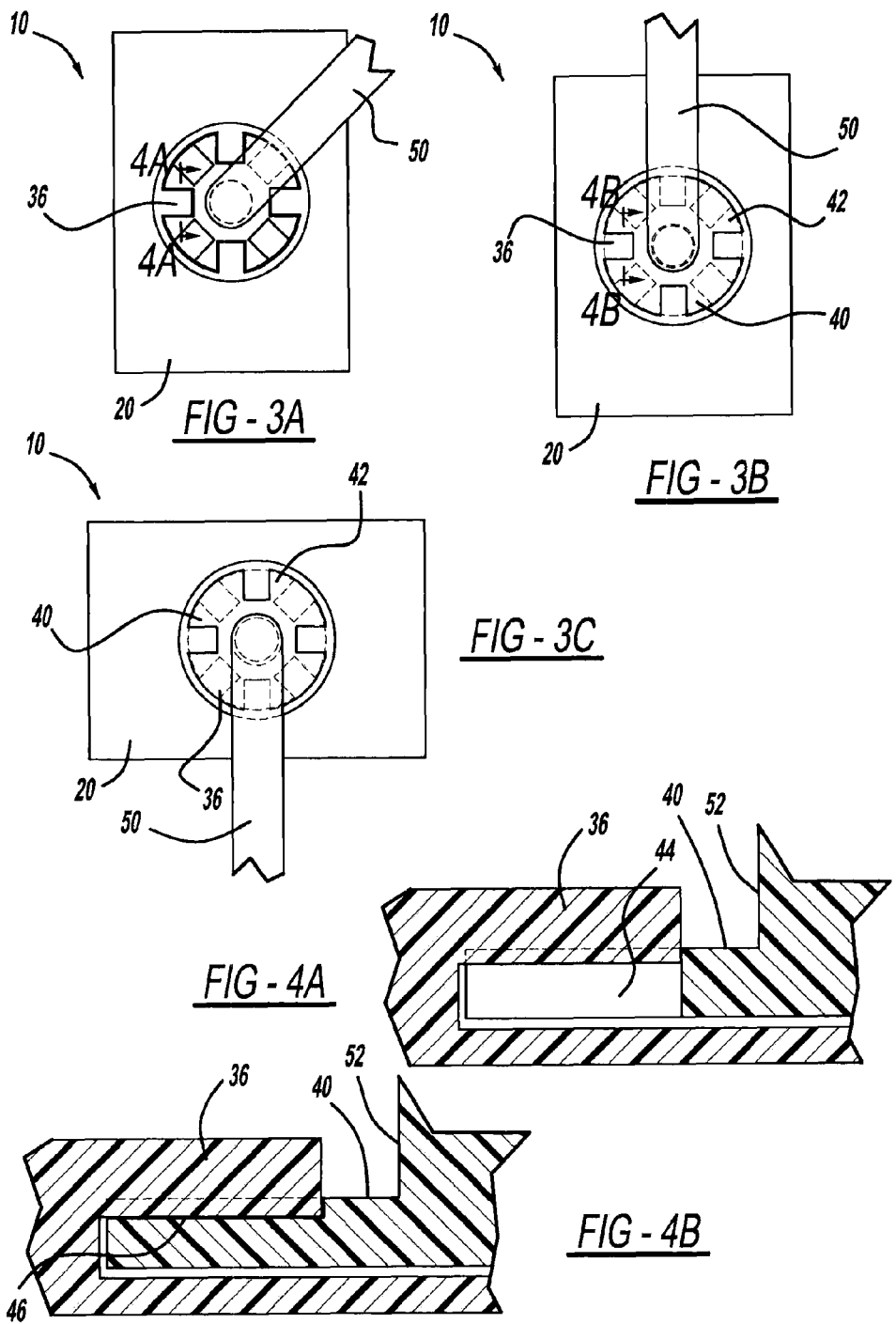

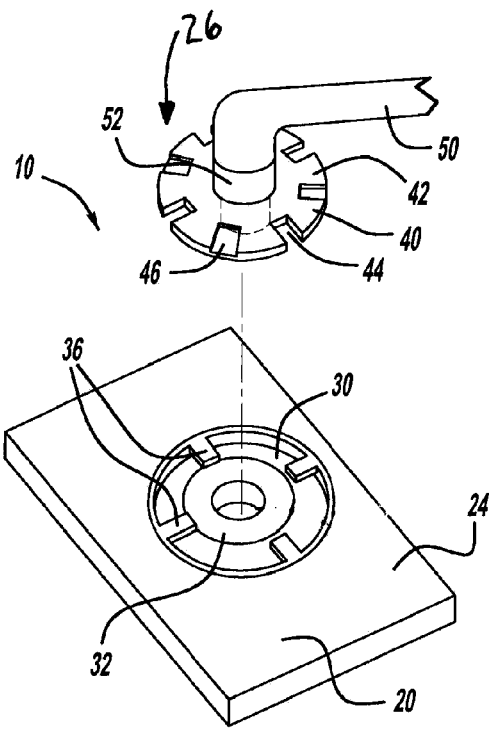
FIG - 5
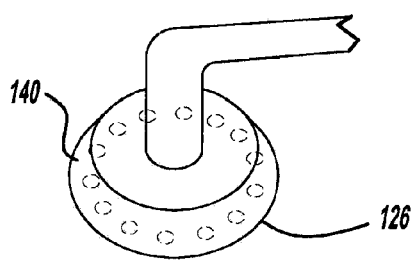
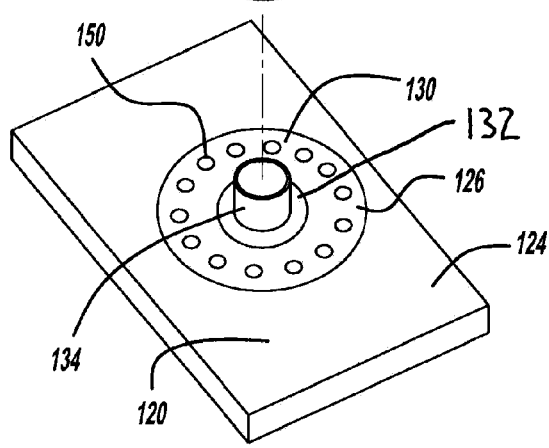
FIG - 6
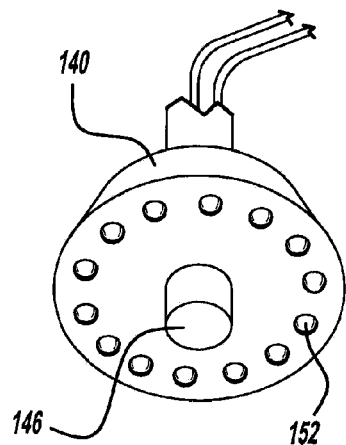
FIG - 7

DIGITAL RADIOGRAPHY SENSORS

BACKGROUND OF THE INVENTION

The present invention relates to digital radiography (X-ray) sensors designed for use in a filmless radiography system and, more particularly, to rotatable and/or detachable digital X-ray sensors.

While the present invention is considered to be applicable to both the medical and dental professions, for example, for ease in description, the following discussion will focus on an intraoral embodiment of the present invention.

Dentists and oral surgeons typically use x-radiation ("X-rays") to obtain images of their patients' teeth, mouths and gums to aid in diagnosis and treatment. In traditional oral and dental radiography, a cartridge containing a piece of photographic film is placed in the patient's mouth, for example, behind a patient's tooth, and an X-ray beam is projected through the tooth and onto the film. The film, after being exposed in this manner, is developed in a dark room or a closed processor using special chemicals to obtain a photographic image of the tooth.

More recently, the field of filmless dental radiography has emerged. In filmless dental radiography, an X-ray beam is still projected through the target area such as a patient's tooth, but no photographic film is used. Instead, an electronic sensor is placed in the patient's mouth behind the tooth to be examined. The electronic sensor may include a charge-coupled device (CCD) or any other filmless radiation sensor. The X-rays pass through the tooth and impinge on the electronic sensor, which converts the X-rays into an electrical signal. The electrical signal is transmitted over a wire to a computer, either directly or through a module containing intermediate processing circuitry. The computer then processes the signal to produce an image on an associated output device, such as a monitor or a printer.

Filmless dental radiography offers several advantages over traditional film-based radiography. Most importantly, the electronic sensor is much more sensitive to X-rays than is film, allowing the dosage of X-rays to the patient to be lowered by as much as 90%. Also, the image of the tooth is generated by the computer almost instantaneously, thus eliminating the entire developing process, including the use of potentially harmful chemicals. In addition, because the images are generated electronically, they can be stored electronically in a computer database. Examples of filmless dental radiography systems include those described in U.S. Pat. No. 4,160,997 to Robert Schwartz and U.S. Pat. No. 5,434,418 to David Schick. Filmless dental radiograph systems typically utilize a standard desktop computer, such as an IBM or IBM compatible type personal computer.

Recently, various sensors have been developed which are directed to improve the fit and/or performance of sensors within the oral cavity. However, even with the more advanced sensors, typically at least two different sized sensors are necessary to obtain a complete X-ray set of a single patient. Bitewing X-rays are a vital part of any diagnosis and are often the most widely taken X-ray. Periapical X-rays are generally taken for specific diagnosis of dental pathology, particularly for an issue with the tooth root and bone structure supporting the tooth.

Even using different sized sensors, the known sensors are often inadequate at taking full tooth X-rays including the root. Furthermore, often the fixed cable extending from the sensor makes it difficult to properly position the sensor within the oral cavity. Thus, the present invention allows for better sensor placement within the oral cavity which will allow the dental staff to capture better X-ray images.

SUMMARY OF THE INVENTION

The present invention provides an intraoral sensor which is rotatable for proper positioning within a dental patient's oral cavity without significant interference from the cable which is connected to a computer or module containing intermediate processing circuitry. As a result, the intraoral sensor is configured to fit comfortably and in closer proximity to a target area in an intraoral cavity than currently known static sensor and cable corrections. By allowing for rotation of the sensor, not only does the sensor fit more comfortably, but the sensor can be positioned to capture a greater image of the teeth, including the roots or other targeted areas, such as bone structure. These features are believed to reduce refractive error in the image received by the sensor, thereby improving the image data transmitted by the sensor. Preferably, the sensor is selectively detachable from the cable leading to the computer and/or image display unit. Thus, unlike presently known filmless X-ray sensors, if either the cable or the sensor becomes damaged, they can be readily replaced.

Still further, the preferred configuration of the sensor is relatively thin, which also contributes to the improved ergonomics of the sensor, and enables the sensor to get closer to the target area of an oral cavity, thereby improving the image data transmitted by the sensor.

Further features of the present invention will become apparent from the following detailed description taken with reference to the accompanying drawings.

BRIEF DESCRIPTION OF THE DRAWINGS

The present invention will become more fully understood from the detailed description and the accompanying drawings, wherein:

FIG. 1 is an exploded perspective views of a sensor assembly according to a first embodiment of the present invention;

FIG. 2 is an exploded perspective view of a sensor assembly according to a second embodiment of the present invention;

FIGS. 3A-3C are top views of the sensor assembly shown in an installation position as well as first and second installed positions;

FIG. 4A is a cut-away view showing the sensor head and cable in an installation position;

FIG. 4B is a cut-away view showing the sensor head and cable in an installed position;

FIG. 5 is a perspective view of a sensor assembly according to a third embodiment of the present invention;

FIG. 6 is a perspective view of a sensor assembly according to a fourth embodiment of the present invention;

FIG. 7 is a perspective view of a sensor assembly according to a fifth embodiment of the present invention;

DETAILED DESCRIPTION OF THE PREFERRED EMBODIMENTS

Figure 10:
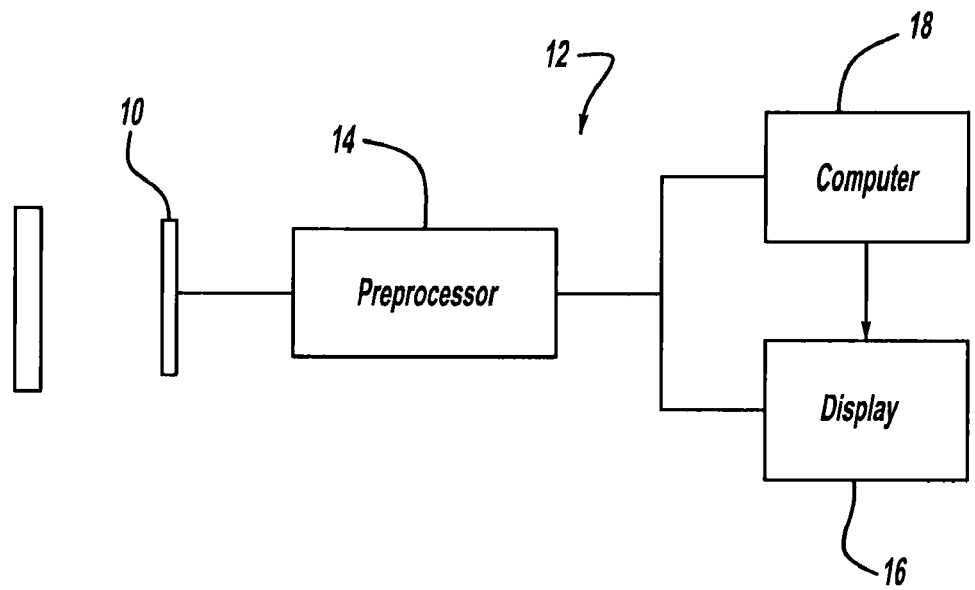
FIG. 10 is a schematic representation of a filmless radiography system using a sensor according to the teachings of the present invention.

A sensor according to the present invention is designed to be used with a filmless radiography system. As an example, a sensor 10 according to the present invention can be used as part of a filmless radiography system 12 which is designed according to the principles of Schwartz U.S. Pat. No. 4,160, 997 (Schwartz patent), which is incorporated hereby by reference. As illustrated in FIG. 10, the sensor 10 transmits digital image data to a preprocessor 14, and the preprocessor transmits the image data either directly to a display device 16, or to a computer 18 which is connected to the display device 16. The preprocessor 14 is configured to normalize the image data transmitted by the sensor 10, to improve the contrast (color and/or grayscale) of such data in relation to the raw image data produced by the sensor. The image data is then transmitted directly to the display device 16, or the image data is transmitted to the computer 18 which can manipulate the image data on the display device. The manner in which the image is processed, transmitted and/or displayed can be in accordance with the principles of the Schwartz patent, or in accordance with other well known devices and systems for processing and displaying the image data. Such devices and systems are well known to those in the art and should not require further explanation.

In addition, the sensor 10 has internal structure, which is designed in accordance with the principles of the Schwartz patent. The internal structure includes components which receive radiated energy image data from a target area of an intraoral cavity (e.g. X-ray images of a patient's teeth, gums, etc), convert the resulting X-ray image data into a visible light image, and transmit the visible light image to a charge coupled device (CCD) or any other visible light sensor forming part of the structure.

As noted in U.S. Pat. No. 6,652,141 B1 to Cianciosi, which is hereby incorporated by reference, the internal structure is suggested to include an array of CCD detectors, a printed circuit board associated with the CCD detectors, and a radiant energy screen with the appropriate coating to convert a radiant energy image to a visible image that impinges on the CCD detectors. The printed circuit board is coupled to a cable 50, as shown in FIG. 1 for example, which transmits the image data from the CCD array to the preprocessor 14 which preprocesses and transmits the image data to the display device 16 and/or to the computer 18. Again, the internal structure of the sensor can be constructed in various known ways, and should not require further explanation to those in the art.

The basic configuration for a sensor assembly 10 according to the present invention as disclosed with reference to FIGS. 1-4B. In FIG. 5, the sensor assembly 10 comprises a sensor body (or housing) 20 configured to fit in a patient's oral cavity proximate a target area of the oral cavity. The sensor body 20 houses the CCD detectors, circuit board and radiant energy screen examples of which are described in U.S. Pat. No. 6,652,141 which is hereby incorporated by reference by way of non-limiting example. The side of the sensor body which is disposed adjacent to the target area of the teeth and/or jaw line, is generally formed from a biocompatible material that is transparent to X-ray energy. The side of the sensor body 24 which hosts the rotatable connector assembly 26 can be formed, for example, from a biocompatible thermoplastic material which is not transparent to X-ray energy. The side sections at the sensor body are bonded or otherwise fastened together, and enclose the internal structure components of the sensor.

The rotatable connector assembly 26 is in the form of either a male or female component 30 which mates with a complementary male or female component 40 disposed along the terminal portion 52 of the electrical cable 50. More particularly, according to the embodiment depicted in FIG. 1, the component 30 is a male component including a well 32 having an upwardly projecting post 34 which seats within a central recess (not shown) contained on the component 40. The component 40, as shown, includes a radially extending flange 42 having cut-out portions 44 (holes) for assembling the components 30 and 40 to complete the necessary circuit for conveying the digital image data. The cut-out portions 44 are fit over the inwardly projecting tabs 36 and the sensor is rotated such that the ace 46 of the flange 42 is held in place under the tabs 36, which extend radially inwardly over the well thereby holding the components 30 and 40 in contact to allow for image data communication. As shown in the embodiment of FIGS. 2 and 4B, the flange 42 may include spaced apart recesses 46 into which the tabs 36 insert to better secure the body 20 and cable 50 together. Additionally, to enhance contact between the sensor body 20 and the cable 50, either a portion of the post 34 or the receiving end 52 of the cable 50 into which the post is inserted may be magnetized to facilitate magnetic coupling in addition to the mechanical attachment.

FIGS. 3A-3C show the connection between the sensor body 20 and the connecting cable at various stages of the installation process. For example, FIG. 3A shows the flange 42 positioned such that the cut out portions 44 pass over the tabs 36. FIG. 3B shows the sensor body rotated 45° such that the sensor body 20 is fixed in a position whereby the cable 50 extends beyond one end of the generally rectangular sensor body. FIG. 3C, in contrast, shows the sensor body 20 rotated 45° in the opposite direction such that the cable 50 extends beyond one side of the upper body. Further reference can be made to FIGS. 4A-4B which show the flange 42 installed into the well 32 in both the insertion position and the installed positions, respectively.

As shall be understood by those skilled in the art, the embodiments of FIGS. 1 and 2 (along with the assorted detailed figures) can be formed such that the male and female connections are alternatively disposed on the sensor body and cable as shown in FIG. 5.

Referring to FIG. 6, an alternative rotatable intraoral sensor 120 is illustrated as including connector assembly 126 having a male portion 130 located along the side 124 of the sensor body 120 and a female portion 140 associated with the cable 50. Hereto, the male portion includes a post 134 which seats within a female receptacle of the female portion 140 to complete the image data circuit upon sufficient connection. Again, the opposing male/female relationship is contemplated according to FIG. 7. In addition to the male/female coupling of the embodiments of FIGS. 6 and 7, an added feature includes detents 150 and mating protrusions 152 which seat within the detents when the sensor body is apportionately rotated relative to the cable. As can be appreciated, the embodiments of FIGS. 6 and 7 allow for incremental rotation of the sensor body relative to the cable position and thus the cable can extend via the connection at various positions from the sensor body. The sensor assembly embodiments of FIGS. 6 and 7 are believed to be particularly suited for magnetic coupling between the flange 140 and the well 132, over and above the mechanical coupling occurring at the post interface of the 134 and female receptacle of the female portion 140.

Figure 8A:
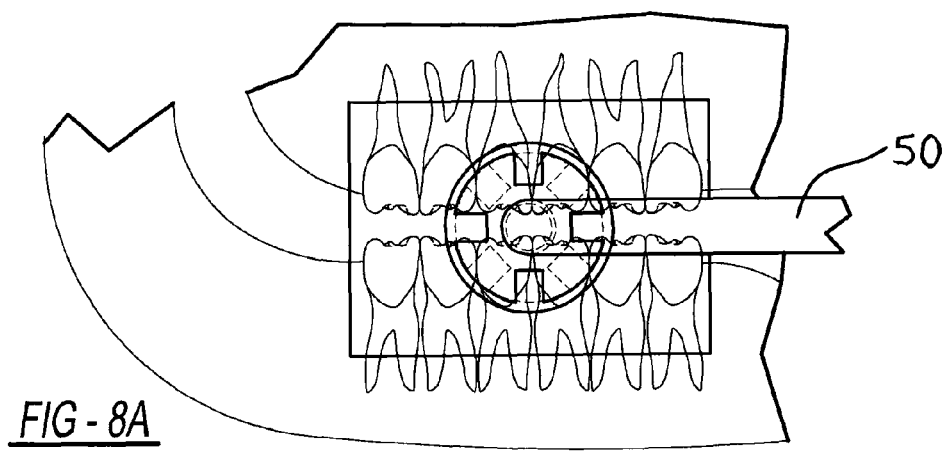
FIGS. 8A-8C demonstrate the rotatable nature of the sensor assemblies for repositioning of a sensor for elongated or wide angle views.
Figure 8B:
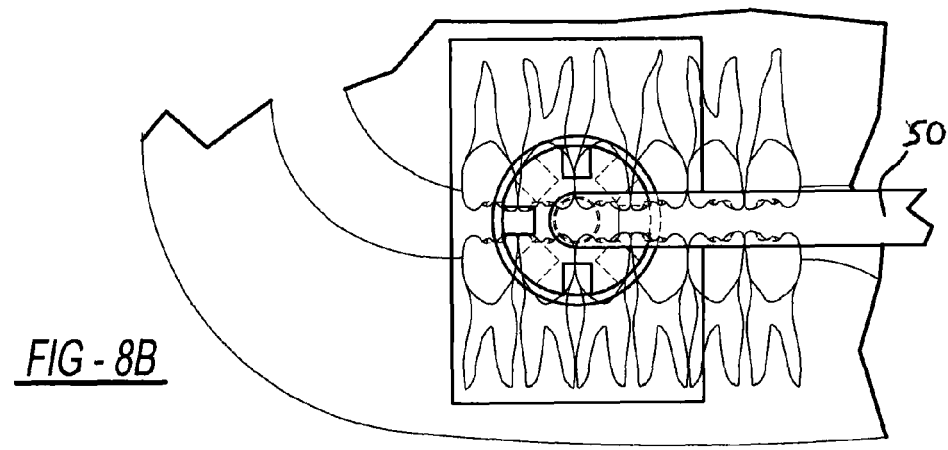
Figure 8C:
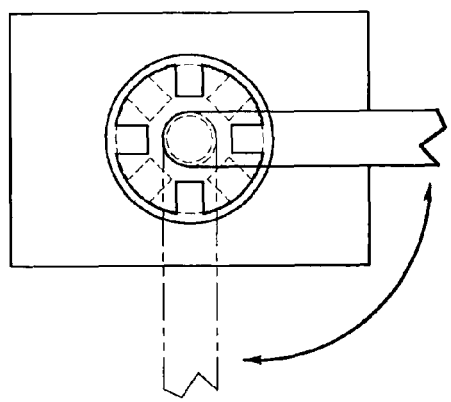

A major problem with prior art X-ray sensor embodiments which is addressed by the present invention is illustrated with reference to FIGS. 8A-8C. For example, when currently known X-ray sensors are employed in the posterior region of an intraoral cavity, particularly when a full tooth X-ray is desired, the connector cable 50 interferes with the oral cavity due to the rigid connection between the cable and the sensor body making it difficult to obtain an accurate X-ray. By rotating the sensor relative to the cable as shown in FIG. 8C, not only is there sufficient clearance for the cable, but a full tooth X-ray is also possible.

Figure 9:
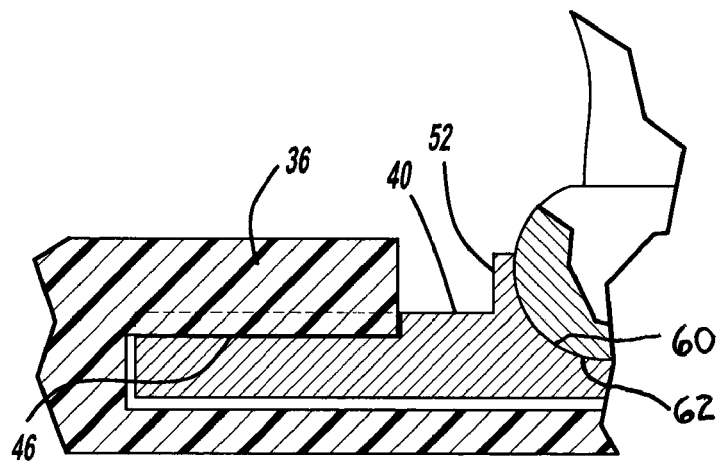
FIG. 9 is a cut away side view of a sensor assembly according to a fifth embodiment of the present invention.

As shown, in FIG. 9, yet another embodiment of the present invention is depicted. According to this embodiment, the coupling between the sensor body and the cable are accomplished via a ball and socket design which is intended to allow for a free swivel-type rotation of the sensor body relative to the cable. This should allow for clearance of the cable without the need for removing the sensor from the mouth and rotating the body prior to re-insertion to an X-ray target area. As shown, a flange similar to that shown in FIGS. 1-5 has a socket 60 for receiving a ball bearing 62 disposed along the terminal end of the cable. Alternatively, the sensor body may include a projecting ball bearing assembly which seats within a socket provided along the terminal end of the sensor cable.

Preferably, the sensing bodies of the various embodiments are positioned so that when the sensor is properly positioned relative to a target area, the sensing structure will receive X-ray energy at about 90° to the direction of the X-ray energy. By providing a comfortable fit relative to the target areas, the sensors are ergonomically improved, in terms of its comfort and feel to a dental patient. In addition, the configuration of the sensor is designed to allow the sensor to be placed closer to a target area in an oral cavity than prior sensors (i.e. closer to target teeth, gum, etc). This feature, and the fact that when the sensor is properly positioned relative to a target area the X-ray energy will by received by the sensing structure at about 90° to the direction of the X-rays is believed to reduce refractive error in the image received by the sensor, thereby improving the image data transmitted by the sensor. Still further, preferred embodiments of the sensor body are relatively thin (e.g. with a thickness of about 5 mm), which also contributes to the improved ergonomics of the sensor, and enables the sensor to get closer to the target area of an oral cavity, thereby improving the image data transmitted by the sensor.

In addition to the advantages of rotation of the sensor body relative to the sensor cable, it should be noted that the numerous embodiments of the present invention allow for quick disconnect-type coupling of the sensor body and cable. This feature allows for the replacement of either the cable or the sensor body if they are dysfunctional, without having to discard the entire assembly which is currently the case in the industry and is unduly expensive.

Accordingly, the foregoing disclosure provides sensor configurations which are particularly useful as a filmless radiography sensor. With the foregoing disclosure in mind, the manner in which the principles of the invention can be used to form various types of intraoral sensors for various uses comparable to filmless radiography will be apparent to those in the art.

What is claimed is:

1. A digital radiography sensor assembly, comprising a sensor body including components for generating radiography image data, and a sensor cable leading from the sensor body to either a computer which reads the data generated by the components or an image display unit, whereby said sensor body is coupled to the sensor cable via selectively disengageable male and female connectors,
   wherein said sensor body is selectively rotatable relative to the sensor cable, and
   wherein said male connector is disposed on the sensor body and includes a post and said female connector includes a socket occurring along a terminal end of the cable for receiving the post.

2. The digital radiography sensor assembly of claim 1, wherein said terminal end of said cable includes a radially extending flange and said sensor body includes a well for receiving said flange.

3. The digital radiography sensor assembly of claim 2, wherein said well includes a plurality of overhanging tabs for locking said flange thereunder within said well.

4. The digital radiography sensor assembly of claim 3, wherein said flange includes a plurality of cut-outs which pass over said overhanging tabs whereby upon rotation of said sensor body relative to the cable the flange is secured under the tabs.

5. The digital radiography sensor assembly of claim 4, wherein said flange includes a recess occurring between the cut-outs, said recess shaped to mate with said tabs upon sufficient rotation of the sensor body relative to said cable.

6. The digital radiography sensor assembly of claim 1, wherein said sensor body and said sensor cable are magnetically coupled.

7. The digital radiography sensor assembly of claim 1, wherein the sensor body includes a plurality of spaced apart detents which are engaged by protrusions occurring along a radially extending flange occurring on a terminal end of said cable, said detents and protrusions being of sufficient number to allow for incremental rotation of the sensor body relative to the cable.

8. A digital radiography sensor assembly, comprising a sensor body including components for generating radiography image data, and a sensor cable leading from the sensor body to either a computer which reads the data generated by the components or an image display unit, whereby said sensor body is coupled to the sensor cable via selectively disengageable male and female connectors,
   wherein said sensor body is selectively rotatable relative to the sensor cable, and
   wherein said male connector is disposed on a terminal end of the cable and includes a post and said female connector includes a socket in the sensor body for receiving the post.

9. The digital radiography sensor assembly of claim 8, wherein said male connector includes a ball receivable in the socket and able to swivel when fully engaged therein.

10. The digital radiography sensor assembly of claim 8, wherein said sensor body and said sensor cable are magnetically coupled.

11. A digital radiography sensor assembly, comprising a sensor body including components for generating radiography image data, and a sensor cable leading from the sensor body to either a computer which reads the data generated by the components or an image display unit, whereby said sensor body is coupled to the sensor cable via selectively disengageable male and female connectors,
   wherein said sensor body and said sensor cable are magnetically coupled.

12. The digital radiography sensor assembly of claim 11, wherein said male connector is disposed on the sensor body and includes a post and said female connector includes a socket occurring along a terminal end of the sensor cable for receiving the post.

13. The digital radiography sensor assembly of claim 11, wherein a terminal end of said sensor cable includes a radially extending flange and said sensor body includes a well for receiving said flange.

14. The digital radiography sensor assembly of claim 13, wherein said well includes a plurality of overhanging tabs for locking said flange thereunder within said well.

15. The digital radiography sensor assembly of claim 14, wherein said flange includes a plurality of cut-outs which pass over said overhanging tabs whereby upon rotation of said sensor body relative to the cable the flange is secured under the tabs.

16. The digital radiography sensor assembly of claim 15, wherein said flange includes a recess occurring between the cut-outs, said recess shaped to mate with said tabs upon sufficient rotation of the sensor body relative to said cable.

17. The digital radiography sensor assembly of claim 11, wherein the sensor body includes a plurality of spaced apart detents which are engaged by protrusions occurring along a radially extending flange occurring on the terminal end of said cable, said detents and protrusions being of sufficient number to allow for incremental rotation of the sensor body relative to the cable.

18. The digital radiography sensor assembly of claim 11, wherein said sensor body is selectively rotatable relative to the sensor cable.

19. The digital radiography sensor assembly of claim 11, wherein said male and female connectors are in the form of a swiveling ball and a socket.

* * * * *